US00PP24394P2

(12) United States Plant Patent
Simpson

(10) Patent No.: US PP24,394 P2
(45) Date of Patent: Apr. 22, 2014

(54) STRAWBERRY PLANT NAMED 'MAYFLOWER'

(50) Latin Name: *Fragaria×ananassa*
Varietal Denomination: Mayflower

(75) Inventor: David W. Simpson, Kent (GB)

(73) Assignee: East Mailing Research, Kent (GB)

( * ) Notice: Subject to any disclaimer, the term of this patent is extended or adjusted under 35 U.S.C. 154(b) by 223 days.

(21) Appl. No.: 13/385,359

(22) Filed: Feb. 15, 2012

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Penny J. Aguirre

(57) ABSTRACT

A new and distinct cultivar of strawberry plant 'Mayflower' characterized by its firm berries that are tolerant to rain, and bright red in color and by its vigorous growth habit with tolerance to *Phytophthora cactorum.*

6 Drawing Sheets

Botanical classification: *Fragaria×ananassa.*
Variety denomination: 'Mayflower'.

BACKGROUND OF THE INVENTION

The present invention includes a new and distinct cultivar of *Fragaria×ananassa* named 'Mayflower', and will herein be referred to as 'Mayflower'.

The new variety resulted from an ongoing breeding program in Kent, United Kingdom. The objectives of the breeding program were to produce a strawberry plant that produced large, firm berries with a high yield and plants that were disease resistant.

'Mayflower' arose from a controlled cross made by the Inventor in 1996 between unnamed strawberry plants from the Inventor's breeding program designated as accession number EM-639 as the female parent and accession number ITA 80-52-1 as the male parent. 'Mayflower', originally designated as accession number EM-995, was selected as a single unique plant in June 1997 from amongst the seedlings that resulted from the above cross.

Asexual reproduction of the new cultivar was first accomplished by rooting of stolons by the Inventor in Kent, United Kingdom. Repeated propagation has shown that the unique characteristics of 'Mayflower' are stable and reproduced true to type in successive generations.

BRIEF SUMMARY OF THE INVENTION

The following traits have been repeatedly observed and are determined to be characteristics of the new cultivar of strawberry. These attributes in combination distinguish 'Mayflower' as unique from all other strawberry cultivars known to the Inventor.

1. 'Mayflower' exhibits firm berries.
2. 'Mayflower' exhibits berries that are tolerant to rain.
3. 'Mayflower' berries that are bright red in color.
4. 'Mayflower' exhibits good vigor.
5. 'Mayflower' exhibits tolerance to *Phytophthora cactorum.*

'Mayflower' differs from its parent plants in the following characteristics. 'Mayflower' differs from its female parent, EM-639, in having a more upright plant habit and in having larger berries. 'Mayflower' differs from its male parent, ITA 80-52-1, in having larger berries that have a softer flesh texture, and in being more tolerant to *Phytophthora cactorum.* 'Mayflower' can be most closely compared to the cultivar 'Jewel' (U.S. Plant Pat. No. 5,897) and 'Cabot' (U.S. Plant Pat. No. 16,971). 'Mayflower' differs from 'Jewel' in having berries that are lighter red in color, firmer, ripen 4 days later, and that hold its size better throughout the picking season. 'Mayflower' differs from 'Cabot' in having berries that are smaller in size and firmer, in having more leaf cover, and in having a smoother surface. In addition, plants of 'Mayflower' are less compact, runners more freely, and have stolons (runners) that are more pubescent.

BRIEF DESCRIPTION OF THE DRAWINGS

The accompanying color photographs depict the characteristics of two year-old plants of 'Mayflower' and comparison plants as grown under standard field conditions in Whately, Mass. The photographs depict color features as true as is reasonably possible with the digital photography methods used. The color values cited in the detailed botanical description accurately describe the new strawberry.

The photograph in FIG. 1 illustrates a typical plant of 'Mayflower'.

Figure 1:
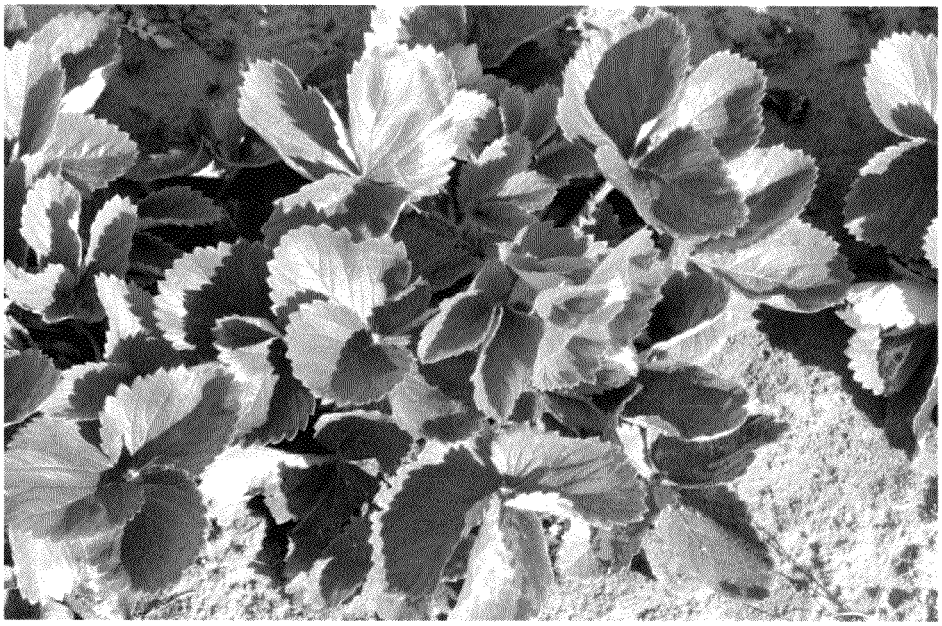
Figure 2:
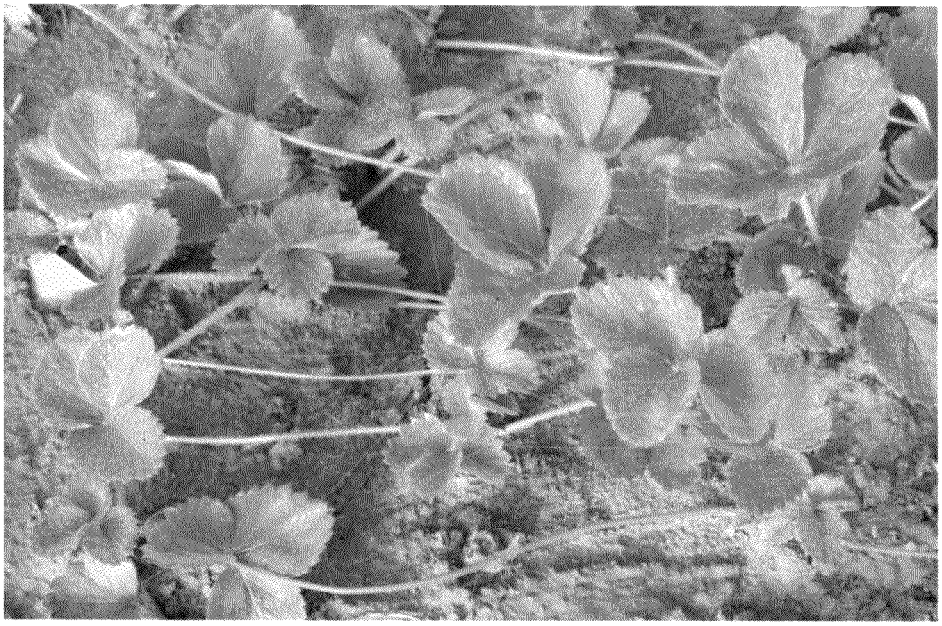

The photograph in FIG. 2 illustrates the stolons of 'Mayflower'.

Figure 3:
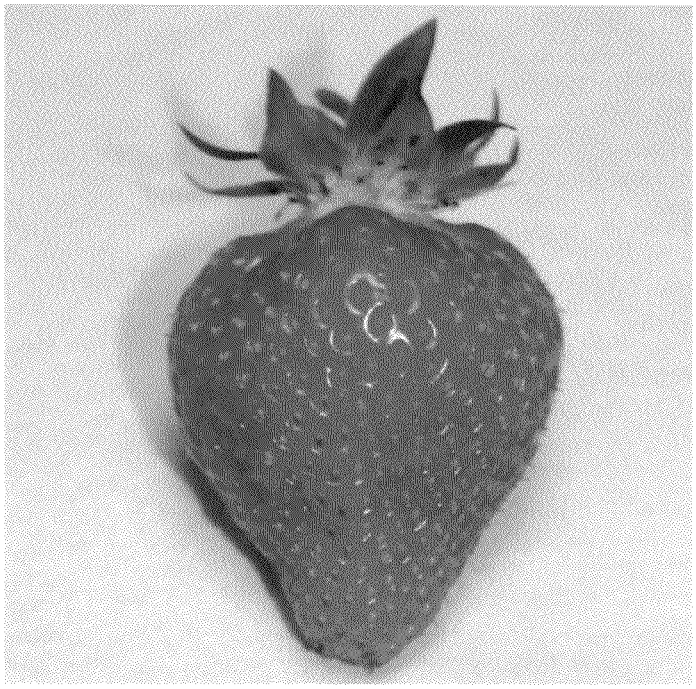

The photograph in FIG. 3 illustrates a typical fruit of 'Mayflower'.

Figure 4:
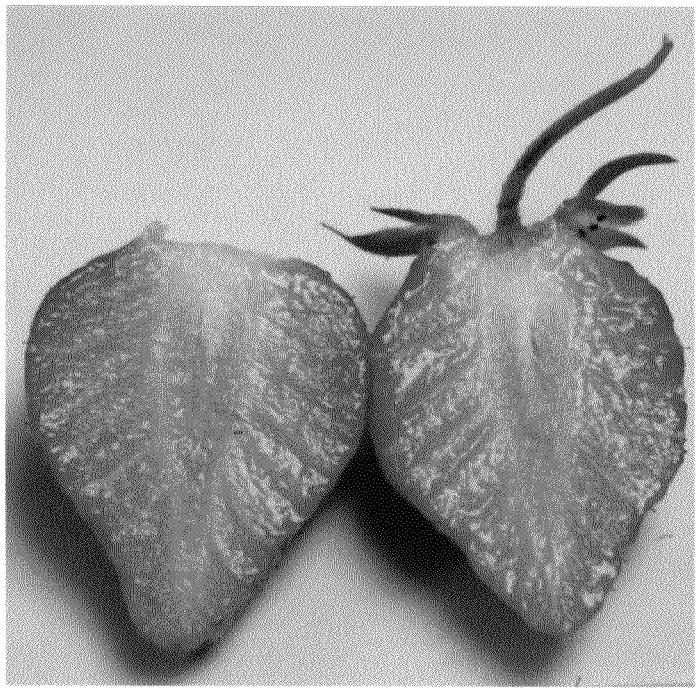

The photograph in FIG. 4 illustrates a cut fruit of 'Mayflower'.

Figure 5:
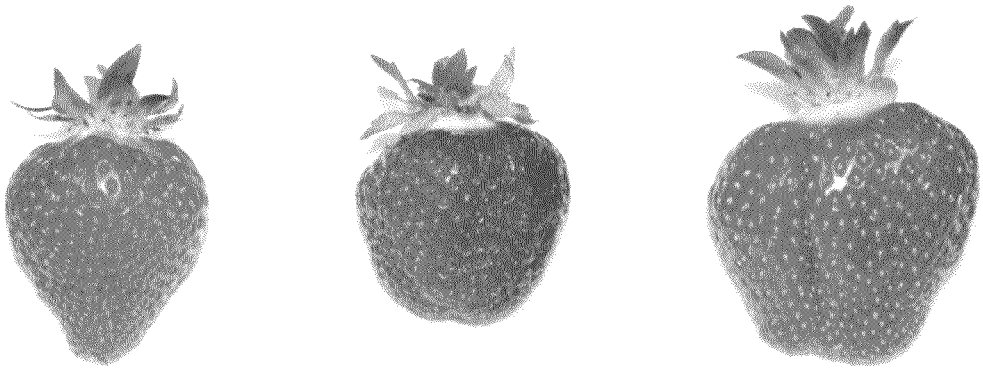

The photograph in FIG. 5 provides a comparison of whole fruit of 'Mayflower' (left), 'Jewel' (center) and 'Cabot' (right).

Figure 6:
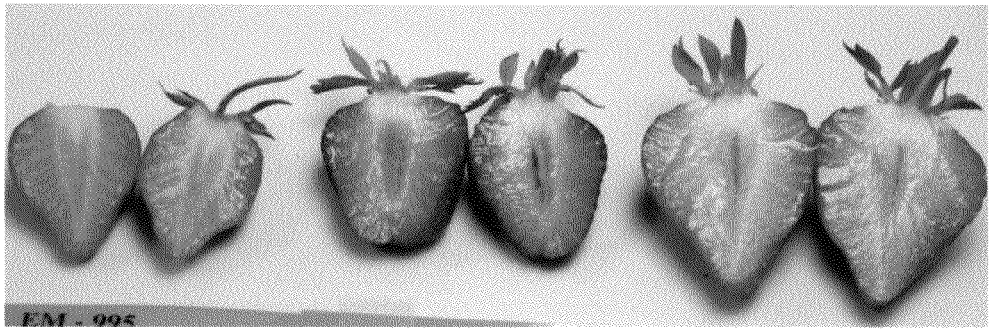

The photograph in FIG. 6 provides a comparison of cut fruit of 'Mayflower' (left), 'Jewel' (center) and 'Cabot' (right).

Figure 7:
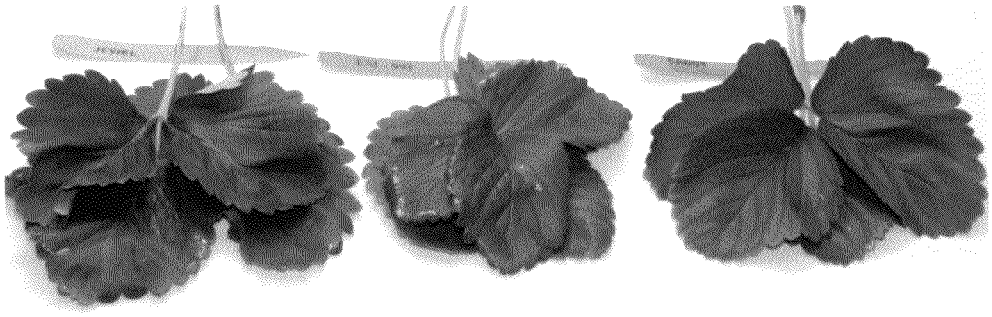

The photograph in FIG. 7 provides a comparison of the foliage of 'Mayflower' (center), 'Jewel' (left) and 'Cabot' (right).

Fingerprint:

Simple sequence repeat markers (SSRs) were used to establish a DNA fingerprint for 'Mayflower'. DNA was extracted from strawberry leaves using a total nucleic acid procedure. The primers and reaction protocols were from Lewers et al., 2005. (Strawberry GenBank-derived and genomic simple sequence repeat (SSR) markers and their utility with strawberry, blackberry, and red and black raspberry. J. Amer. Soc. Hort. Sci. 130(1): 102-115).

The ARSFL numbers designate the individual SSR markers used in this patent application to establish a DNA fingerprint for 'Mayflower'. The primer sets used for the SSR detection, along with their base sequences and Sequence ID NOs submitted in the Sequence Listing, are listed below and correspond to the following Figures.

Figure 8:
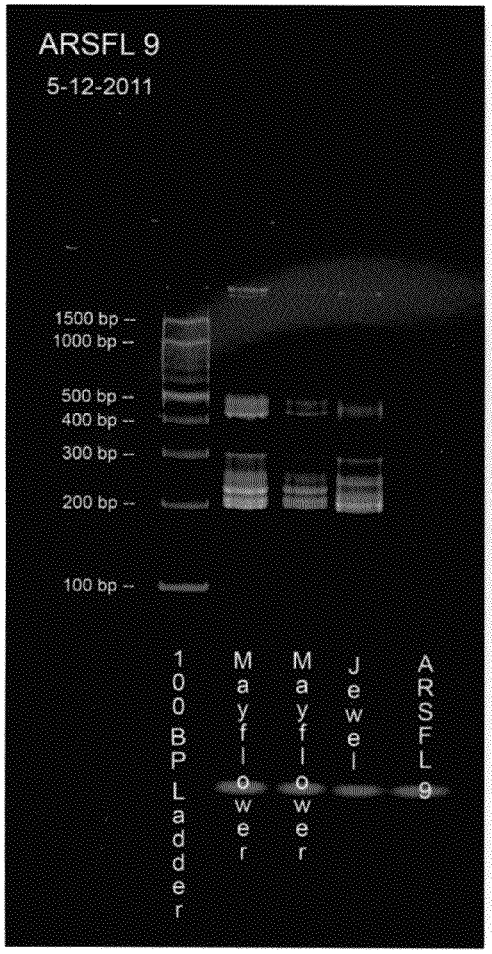

FIG. 8, ARSFL 9: F: gcgaggcgat catggagaga (SEQ ID NO: 1)

R: gcgtttccta cgtcccaata aatc (SEQ ID NO: 2)

Figure 9:
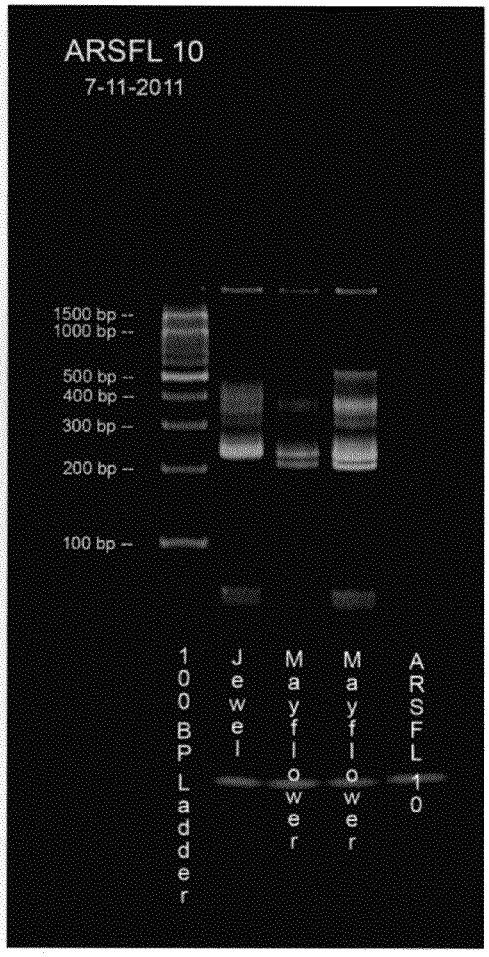

FIG. 9, ARSFL 10: F: gcgtcagccg tagtgatgta gcag (SEQ ID NO: 3)

R: gcgccagccc ctcaaatatc (SEQ ID NO: 4)

Figure 10:
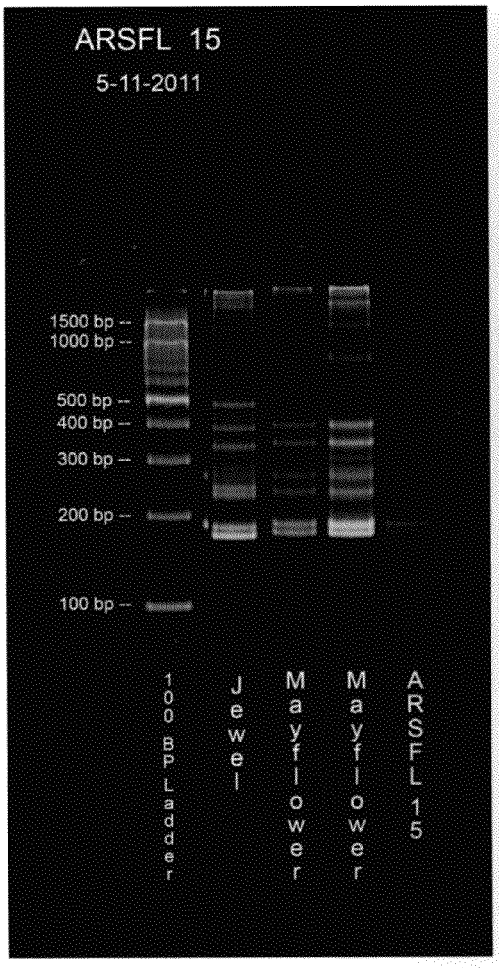

FIG. 10, ARSFL 15: F: gcgggctgtc cacactcctt tct (SEQ ID NO: 5)

R: gcgatgcgta agtctcttca aata (SEQ ID NO: 6)

Figure 11:
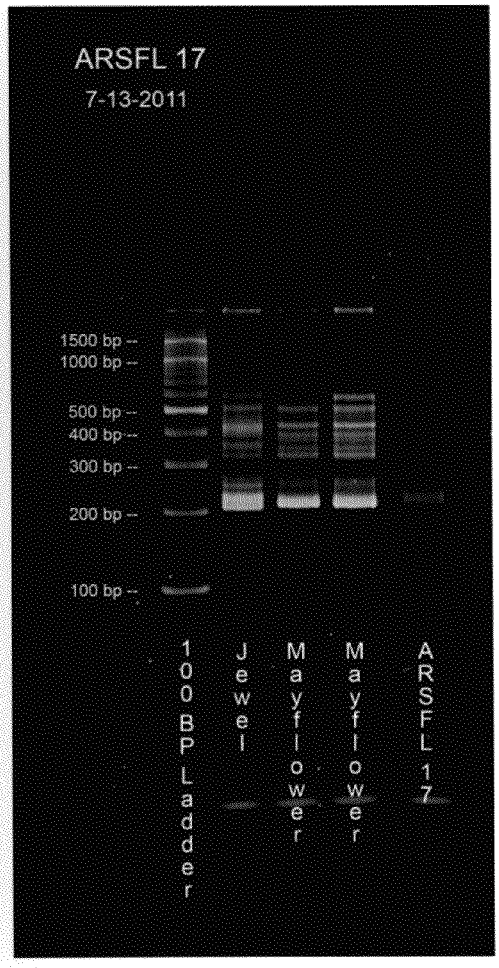

FIG. 11, ARSFL 17: F: gcgcatcaca atcgccatag aaac (SEQ ID NO: 7)

R: gcgaacacgc cttcaacaac cac (SEQ ID NO: 8)

Figure 12:
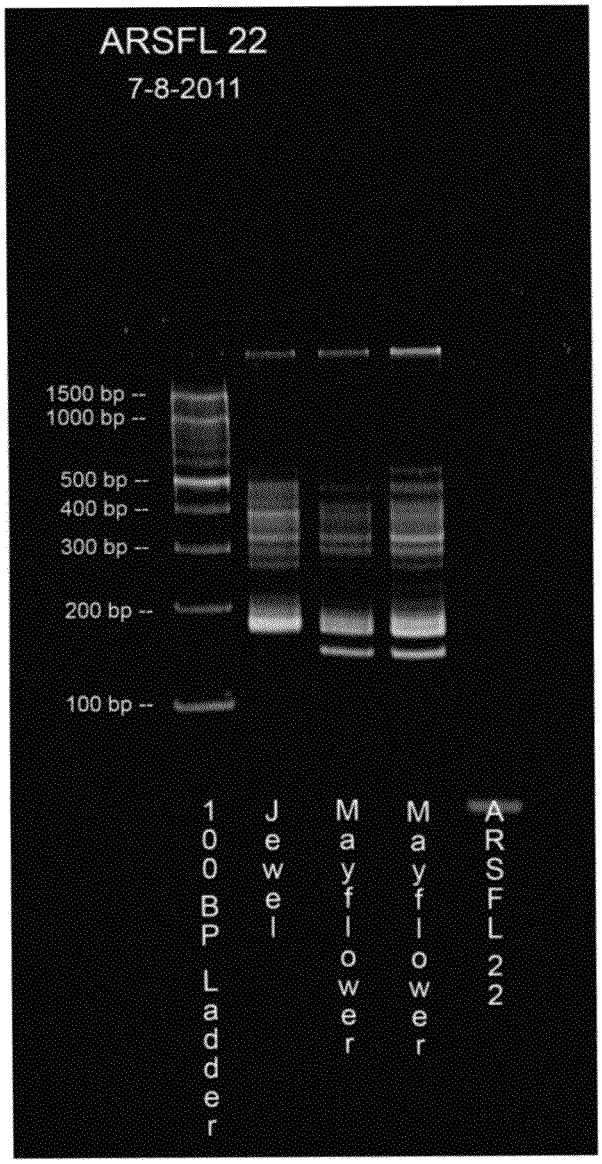

FIG. 12, ARSFL 22: F: gcgaacccca ttaacagctt ca (SEQ ID NO: 9)

R: gcgatcaaat tcccctctaa caat (SEQ ID NO: 10)

Each of these primer sets produces a DNA banding pattern, or fingerprint, for 'Mayflower' that is distinct from the banding pattern for 'Jewel'.

Photos show the DNA banding patterns of 'Mayflower' and 'Jewel' for each SSR marker. The lanes in each photo are aligned as follow from left to right: FIG. 8: Size standard (measuring base pairs), 'Mayflower', duplicate of 'Mayflower', 'Jewel', primer blank. FIG. 9, FIG. 10, FIG. 11, and FIG. 12: Size standard (measuring base pairs), 'Jewel', 'Mayflower', duplicate of 'Mayflower', primer blank.

DETAILED BOTANICAL DESCRIPTION

The botanical data describing was collected on one year-old plants of 'Mayflower' as grown in a garden in New Hope, Minn. and on two-year-old plants grown under standard field conditions in Whately, Mass. The characteristics may vary in detail depending on variations in conditions such as temperature, day-length, light intensity, soil types, and water and fertility levels as 'Mayflower' was not tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Commenced about the 3$^{rd}$ week in may in Whately, Mass.

*Plant type*.—Herbaceous perennial.

*Plant habit*.—Upright and mounded, stoloniferous.

*Height and spread*.—Reaches about 20 cm in width and 30 cm in height.

*Cold hardiness*.—U.S.D.A. Zone 3.

*Environmental stresses*.—Berries have shown to be resistant to rain damage.

*Diseases resistance*.—Tolerance to *Phytophthora cactorum* has been observed.

*Root description*.—Fibrous.

*Propagation*.—Rooting of stolons.

*Growth rate*.—Vigorous.

*Stem description*.—Acaulescent.

*Stolon description*.—An average of 50 cm in length and 2.5 mm in length, 158A In color and flushed with 63D.

Foliage description:

*Leaf division*.—Three leaflets.

*Leaf arrangement*.—Basal.

*Leaf attachment*.—Petiolate.

*Leaflet shape*.—Broadly ovate to rounded.

*Terminal leaflet size*.—Average of 5.3 cm in length and 4.8 cm in width.

*Leaflet margins*.—Serrate to crenate, average of 16 teeth per side on terminal leaflet.

*Angle of terminal leaflet to petiole*.—30 degrees from vertical.

*Leaflet base*.—Oblique.

*Leaflet apex*.—Round.

*Leaflet profile*.—Flat to slightly cupped upward.

*Leaflet interveinal blistering*.—Moderate.

*Leaflet venation*.—Pinnate, upper surface; 137A, lower surface; between 145B and 145C.

*Leaflet surface*.—Glabrous and semi-glossy on upper surface , glaucous on lower surface with pubescent on veins.

*Leaflet color*.—Upper surface 137A, lower surface 138B.

*Petiole*.—Round in shape, average of 10 cm in length and 3 mm in width, pubescent surface, 146C in color.

*Petiolules*.—Round in shape, average of 4 mm in length and 2 mm in width, pubescent surface, 146C in color.

Flower description:

*Inflorescence*.—Truss.

*Inflorescence length*.—Average of 23 cm.

*No. of flowers per truss*.—Average of 8.

*Flower position relative to foliage*.—Beneath level of foliage.

*Flower diameter*.—Average of 3.4 cm.

*Calyx*.—Position even, average of 2.5 cm in diameter.

*Sepals*.—Lanceolate, an average of 9 mm in length and 4 mm in width, puberulent on upper and lower surface, 137B on upper and lower surface, truncate base, acuminate apex.

*Petals*.—Average of 5, average of 1.2 cm in length and 1.2 cm in width, touching, color 155B on upper and lower surface, glabrous on upper and lower surface.

*Peduncle*.—137B in color, pubescent surface, average of 2 cm in length and 3 mm in length.

*Pistils*.—Average of 140, average of 1.1 mm in length, 151C in color at anthesis.

*Stamens*.—Average of 21, average of 2.5 mm in length, anther 21B in color, filaments 150B in color at anthesis, pollen 15C in color.

Fruit description:

*Shape*.—Broadly conical.

*Length*.—Average of 2.5 cm in length and 1.9 cm in width.

*Surface*.—Relatively smooth.

*Calyx position*.—Even to very slightly raised.

*Diameter of calyx relative to fruit diameter*.—Similar to slightly smaller.
*Adherence of calyx*.—Strong.
*Glossiness*.—Even.
*External color* (*skin*).—N34 with some areas a color between N34 and 44A.
*Internal color*.—A blend of N34A and 44A with core area 37A.
*Evenness of color of skin*.—Even.
*Evenness of color of flesh*.—Lighter near core.
*Fruit acidity*.—Medium.
*Fruit sweetness*.—Medium.
*Season of harvest*.—June bearing, mid to late, in Massachusetts.
*Achene color*.—152D without sun exposure with some 59B when exposed to sunlight.
*Insertion of achenes*.—Slightly inserted.
*Achene size*.—1 mm in length and 0.5 mm in width.

SEQUENCE LISTING

```
<160> NUMBER OF SEQ ID NOS: 10

<210> SEQ ID NO 1
<211> LENGTH: 20
<212> TYPE: DNA
<213> ORGANISM: Fragaria x ananassa

<400> SEQUENCE: 1

gcgaggcgat catggagaga                                                20


<210> SEQ ID NO 2
<211> LENGTH: 24
<212> TYPE: DNA
<213> ORGANISM: Fragaria x ananassa

<400> SEQUENCE: 2

gcgtttccta cgtcccaata aatc                                           24


<210> SEQ ID NO 3
<211> LENGTH: 24
<212> TYPE: DNA
<213> ORGANISM: Fragaria x ananassa

<400> SEQUENCE: 3

gcgtcagccg tagtgatgta gcag                                           24


<210> SEQ ID NO 4
<211> LENGTH: 20
<212> TYPE: DNA
<213> ORGANISM: Fragaria x ananassa

<400> SEQUENCE: 4

gcgccagccc ctcaaatatc                                                20


<210> SEQ ID NO 5
<211> LENGTH: 23
<212> TYPE: DNA
<213> ORGANISM: Fragaria x ananassa

<400> SEQUENCE: 5

gcgggctgtc cacactcctt tct                                            23


<210> SEQ ID NO 6
<211> LENGTH: 24
<212> TYPE: DNA
<213> ORGANISM: Fragaria x ananassa

<400> SEQUENCE: 6

gcgatgcgta agtctcttca aata                                           24


<210> SEQ ID NO 7
```

-continued

```
<211> LENGTH: 24
<212> TYPE: DNA
<213> ORGANISM: Fragaria x ananassa

<400> SEQUENCE: 7

gcgcatcaca atcgccatag aaac                                          24


<210> SEQ ID NO 8
<211> LENGTH: 23
<212> TYPE: DNA
<213> ORGANISM: Fragaria x ananassa

<400> SEQUENCE: 8

gcgaacacgc cttcaacaac cac                                           23


<210> SEQ ID NO 9
<211> LENGTH: 22
<212> TYPE: DNA
<213> ORGANISM: Fragaria x ananassa

<400> SEQUENCE: 9

gcgaacccca ttaacagctt ca                                            22


<210> SEQ ID NO 10
<211> LENGTH: 24
<212> TYPE: DNA
<213> ORGANISM: Fragaria x ananassa

<400> SEQUENCE: 10

gcgatcaaat tcccctctaa caat                                          24
```

It is claimed:

1. A new and distinct cultivar of strawberry plant named 'Mayflower' as herein illustrated and described.

* * * * *